United States Patent [19]

Arnold et al.

[11] 4,178,428
[45] Dec. 11, 1979

[54] THERMALLY STABLE ENYNE POLYSULFONE POLYMERS

[75] Inventors: Fred E. Arnold, Centerville; Bruce A. Reinhardt, New Carlisle, both of Ohio

[73] Assignee: The United States of America as represented by the Secretary of the Air Force, Washington, D.C.

[21] Appl. No.: 946,291

[22] Filed: Sep. 27, 1978

[51] Int. Cl.$^2$ ............................................. C08G 75/23
[52] U.S. Cl. ................................ 528/174; 260/30.8 R; 260/607 AR; 428/411; 528/125; 528/126; 528/128
[58] Field of Search ............... 528/174, 125, 126, 128; 260/30.8 R, 607 AR

[56] References Cited

U.S. PATENT DOCUMENTS 4,108,926  12/1978  Arnold et al. ...................... 528/174

Primary Examiner—Lester L. Lee
Attorney, Agent, or Firm—Joseph E. Rusz; Cedric H. Kuhn

[57] ABSTRACT

High molecular weight enyne polysulfone thermoplastics are prepared by the reaction of alkali metal salts of 1,4-bis(3-hydroxyphenyl)-buta-1-ene-3-yne and various aromatic diols with aromatic dihalosulfones. Because of the presence of the enyne moiety in the polymer backbone, the polymer can be lightly crosslinked to provide solvent resistant thermoplastics. The polymers are useful in fabricating graphite thermoplastic composites for structural applications.

9 Claims, No Drawings

THERMALLY STABLE ENYNE POLYSULFONE POLYMERS

RIGHTS OF THE GOVERNMENT

The invention described herein may be manufactured and used by or for the Government of the United States for all governmental purposes without the payment of any royalty.

FIELD OF THE INVENTION

This invention relates to high molecular weight enyne polysulfone thermoplastic polymers. In one aspect it relates to a process for preparing the thermoplastic polymers.

BACKGROUND OF THE INVENTION

In recent years there has been an increase in interest in the utilization of thermoplastics in fabricating fiber-reinforced composites. Thermoplastic matrices offer the possibility of reducing the fabrication costs of advanced structures. The cost reductions are possible because faster and less expensive manufacturing procedures can be followed as compared to those employed with conventional resin matrices.

A problem associated with thermoplastic composites relates to the high fabrication temperatures that are required. Temperatures in excess of 200°–300° F. above the glass transition temperature (Tg) of the thermoplastic material are usually necessary to sufficiently decrease the bulk viscosity for the thermoforming process. The problem becomes more critical as the use temprature of the structural composite is extended since higher use temperatures require thermoplastics with higher glass transition temperatures and consequently higher fabrication temperatures. The disadvantages of using very high processing temperatures (800°–1000° F.) include the unfavorable economics of high temperature tooling and the danger of thermal degradation of the polymer during fabrication.

The use of thermoplastic resins as structural material in aircraft has also been limited because of problems associated with linear polymeric systems. Linear polymers have very low solvent, creep and craze resistance. Solvents normally found around an aircraft or air field, such as hydraulic fluids, brake fluids, paint strippers, and the like, are potential hazards to such systems.

From the foregoing it is seen that the ideal thermoplastic material should meet certain requirements. Thus, the material should be one having a low glass transition temperature for favorable processing, and during fabrication its glass transition temperature should increase so as to extend its use temperature. The thermoplastic material should also have the capability to become lightly crosslinked when thermally treated during fabrication so as to diminish the various solvent induced problems inherent in linear polymeric materials.

It is an object of this invention, therefore, to provide high molecular weight thermoplastic material with a glass transition temperature that advances on thermal treatment.

Another object of the invention is to provide thermoplastic material which lightly crosslinks on thermal treatment.

Other objects and advantages of the invention will become apparent to those skilled in the art upon consideration of the accompanying disclosure.

SUMMARY OF THE INVENTION

The present invention resides in high molecular weight enyne polysulfones which, on thermal or radiation treatment, crosslink by addition reactions. The polysulfones can be represented by the following structural formula:

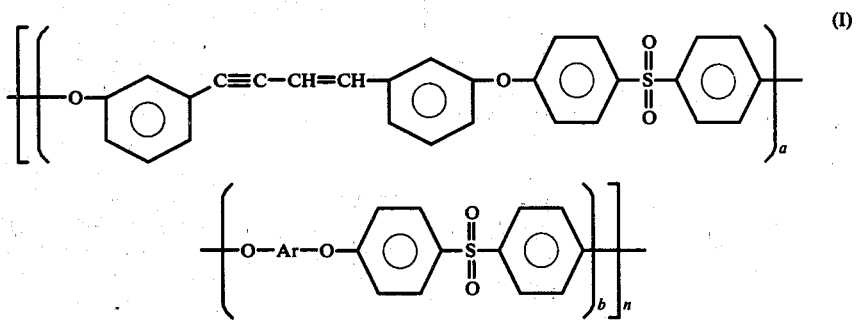

wherein Ar is a divalent aromatic radical; a is equal to 0.05 to 1, b is equal to zero to 0.95, and the sum of a and b is equal to 1; and n is an integer ranging from about 1 to 100. The value of n is usually such that the polymer has an intrinsic viscosity of about 0.10 to 1.5 as determined in N,N-dimethylacetamide at 30° C. Examples of divalent aromatic radicals include the following:

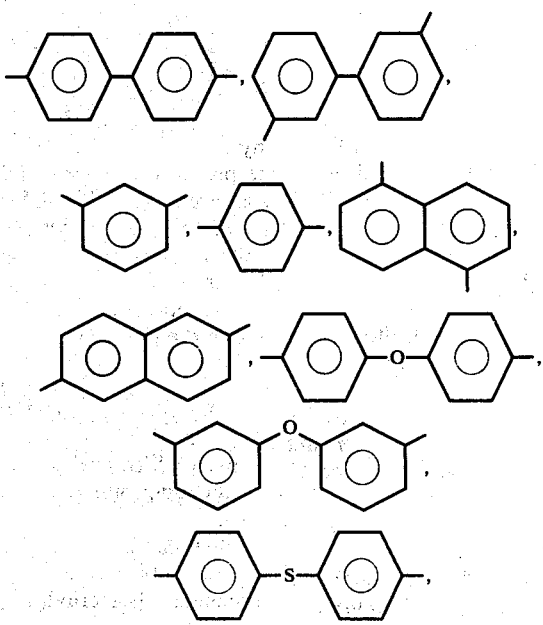

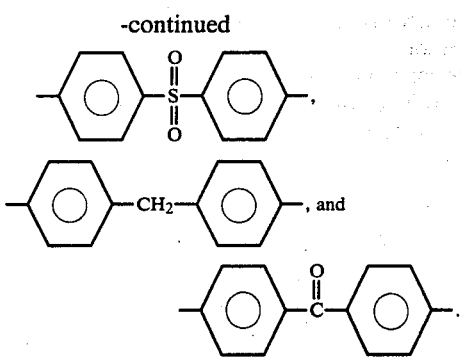

In one embodiment, the present invention resides in the process for preparing the above-defined enyne polysulfones. The reactions involved in carrying out the process are shown by the equations set forth below.

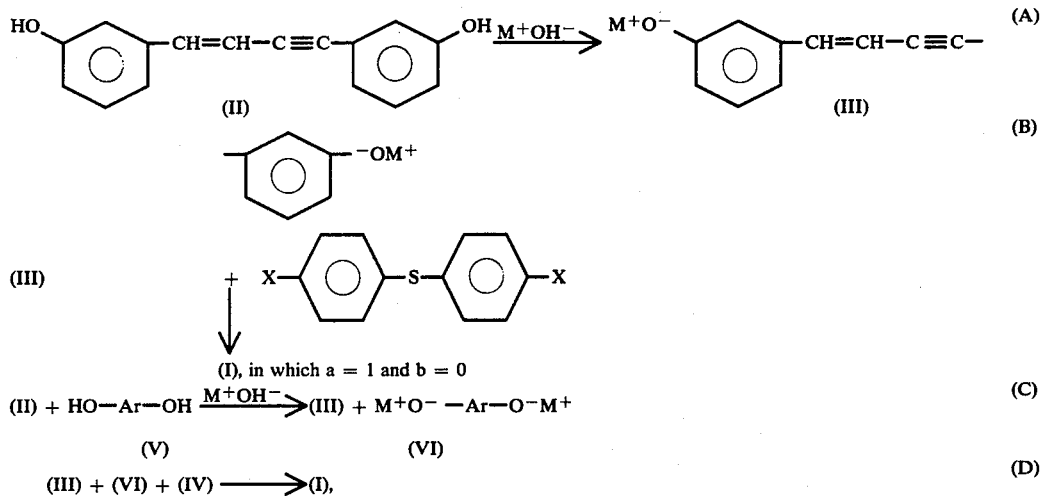

in which a and b are each less than 1 but greater than zero and the sum of a and b equals 1. In the foregoing equations M is an alkali metal, such as potassium or sodium, Ar is a divalent aromatic radical as described above and X is chlorine, bromine, iodine or fluorine.

As seen from equations A and B, when it is desired to prepare an enyne polysulfone according to formula I in which a equals 1 and b equals zero, an alkali metal salt of 1,4-bis-(3-hydroxyphenyl)-buta-1-ene-3-yne (III) is prepared by reacting the bisphenol (II) with a stoichiometric amount of an alkali metal hydroxide, such as potassium, sodium or lithium hydroxide. The formation of the salt is carried out in the presence of a material, such as benzene, which forms an azeotrope with water generated during the reaction. Anhydrous conditions important to the conduct of the process are thereby maintained. The metal salt (III) is then reacted in an aprotic solvent with an equimolar amount of a 4,4'-dihalodiphenylsulfone (IV) to give the polymer of formula I in which a is 1 and b is zero.

The 1,4-bis-(3-hydroxyphenyl)-buta-1-ene-3-yne used in the process is prepared by the procedure described in Example I hereinafter and in commonly assigned copending application Ser. No. 946,290, filed on Sept. 27, 1978. The disclosure of this copending application is incorporated herein by reference.

Examples of aprotic solvents that can be used in the process include dimethylsulfoxide, sulfolane, dimethylacetamide, N,N-dimethylformamide, N-methylprolidone, and the like, as well as mixtures thereof. The condensation reaction is generally conducted at a temperature ranging from about 90° to 200° C. for a period of about 2 to 12 hours. At the end of the reaction period, the product is recovered from the reaction mixture. Recovery of the product is conveniently accomplished by cooling the reaction mixture to room temperature and then pouring the mixture into a non-solvent, such as methanol, thereby causing the polysulfone to precipitate from solution.

When it is desired to prepare an enyne polysulfone according to formula I in which a and b are each less than 1 but greater than zero and the sum of a and b equals 1, the reactions involved are depicted by equations C and D as set forth above. As shown by equation C, a mixture of 1,4-bis(3-hydroxyphenyl)-buta-1-ene-3-yne (II) and an aromatic diol (V) is reacted with an alkali metal hydroxide. As a result of the reaction, a mixture of alkali metal salts (III) and (VI) is formed. According to equation D, the mixture of alkali metal salts is reacted with 4,4'-dihalodiphenylsulfone (IV) to give the aforementioned enyne polysulfone.

The reactions represented by equations C and D are carried out in essentially the same manner as those described above with relation to equations A and B. However, because of the presence of an additional reactant, namely, an alkali metal salt of an aromatic dio (VI), the product (I) contains in its structure a divalent aromatic radical in addition to the enyne ether sulfone moiety. The amount of these groups present in the structure is dependent upon the mole percentages of compounds II and V contained in the reaction mixture used in the reaction shown by equation C. For example, if the reaction mixture contains 50 mole percent of compound II and 50 mole percent of compound V, then a and b are each equal to 0.5. Or if the reaction mixture contains 75 mole percent of compound II and 25 mole percent of compound V, then a is equal to 0.75 and b is equal to 0.25.

Except for the enynediol (II) mentioned above, the starting materials employed in synthesizing the polysulfones are well known compounds that are described in the literature. Examples of aromatic diols (V) that can be used include 4,4'-dihydroxybiphenyl; 3,3'-dihydroxybiphenyl; 1,3-dihydroxybenzene; 1,4-dihydroxybenzene, 1,5-dihydroxynaphthalene; 2,6-dihydroxynaphthalene; 4,4'-dihydroxydiphenylether; 3,3'-dihydroxydiphenylether; 4,4'-dihydroxydiphenylsulfide; 4,4'-dihydroxydiphenylsulfone; 4,4'-dihydroxydiphenylmethane; 4,4'-dihydroxybenzophenone; and the like.

The polymers of this invention are particularly useful for fabricating graphite-reinforced thermoplastic composites. Because of their structure, the polymers when subjected to thermal or radiation treatment undergo interchain reactions to form lightly crosslinked systems that are solvent resistant. The amount of crosslinking can be controlled by adjusting the amount of enyne ether sulfone moiety (a) and divalent aromatic radical (b) in the polymer backbone. The highest crosslink density occurs when a equals 1 and b equals zero. As the value of a decreases and the value of b increases, the crosslink density decreases.

On thermal or radiation treatment and disappearance of the enyne structure, the glass transition temperature (Tg) of the thermoplastic increases. Thus, the enyne groups make possible the utilization of a low Tg for fabrication that advances to a high Tg and use temperature after thermal or radiation treatment.

It is within the scope of the present invention to utilize monofunctional acetylene compounds as reactive plasticizers with the enyne polysulfones. The monofunctional acetylenes lower the Tg of the thermoplastic and then during fabrication become dormant by reacting with the enyne moiety along the polymer backbone. The monofunctional acetylene compounds, which are well known compounds described in the literature, can be represented by the following formula:

R—C≡CH, in which R is a monovalent aliphatic or aromatic radical. Examples of such radicals include $C_xH_{2x+1}$, where x is an integer from 1 to 10, inclusive, 

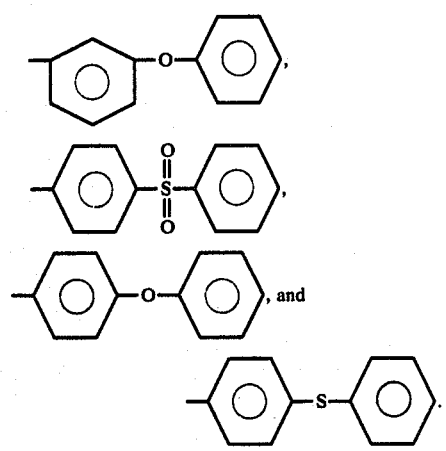

Examples of monofunctional acetylene componds that can be used include 4-chloro-4-(3-ethynylphenoxy)diphenylsulfone, 4-(3-ethynylphenoxy)diphenylsulfone, 3-phenoxyphenylacetylene, 4-ethynyldiphenylsulfone, 4-ethynyldiphenylether, and 4-ethynyldiphenylsulfide. The amount of monofunctional acetylene compound used can vary within rather wide limits, but it is insufficient to react with all of the enyne moieties in the polysulfone structure. In general, the amount used ranges from about 10 to 90 mole percent of the amount of enyne in the polysulfone structure.

Curing of the enyne polysulfones is readily accomplished by heating the materials in an inert or oxidative atmosphere at a temperature ranging from above 250° to 370° C. A heating period of from 1 to 6 hours is usually sufficient to obtain a complete cure although longer times, e.g., up to 24 hours, can be used. While it is not intended to limit the invention to any particular theory, the curing operation is believed to encompass the interchain dimerization of the enyne structure to form cyclooctatetraene. The reaction of the monofunctional acetylene (reactive plasticizer) when admixed with the enyne polysulfone involves a Diels Alder addition reaction with the formation of a triphenylbenzene. The reactions that are believed to occur are shown by the following equations:

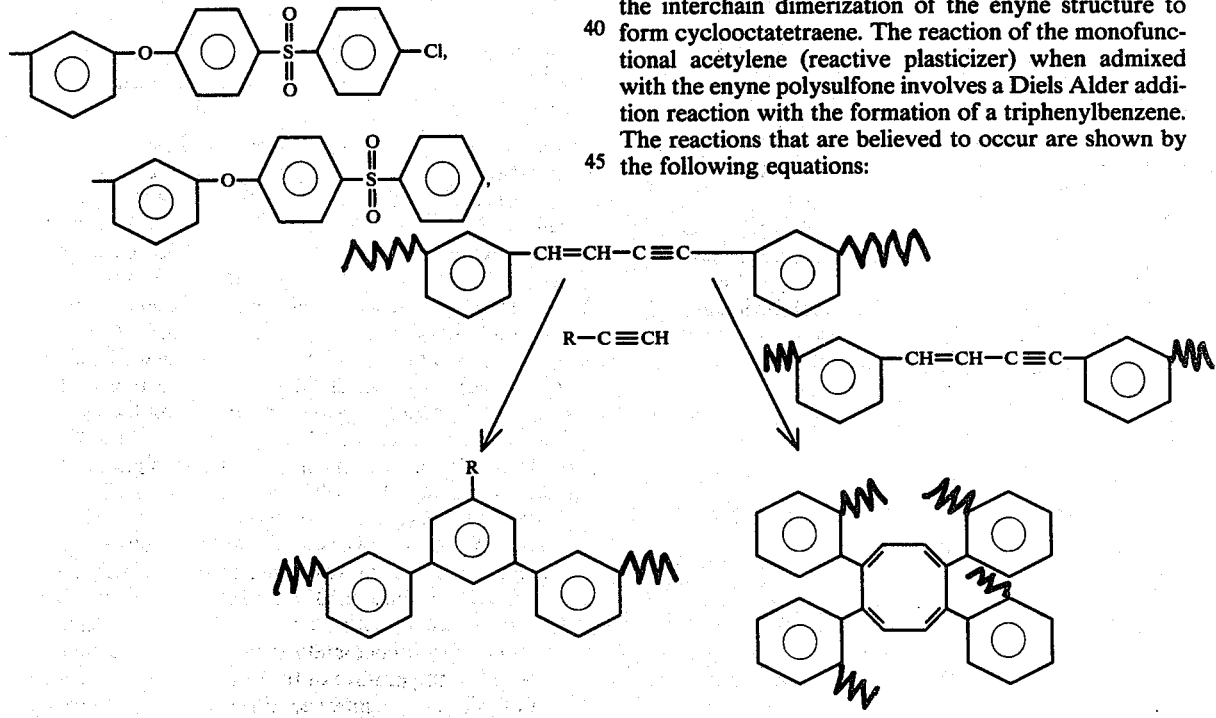

A more complete understanding of the invention can be obtained by referring to the following illustrative examples which are not intended, however, to be unduly limitative of the invention.

EXAMPLE I

Preparation of
1,4-Bis-(3-hydroxyphenyl)-buta-1-ene-3-yne a. 1,4-Bis-[phenyl-(p-toluene sulfonate)]-3-yl-buta-1-ene-3-yne. To a 2-liter, 3-necked round bottom flask, equipped with a nitrogen inlet, condenser and magnetic stirring bar was added 1000 ml glacial acetic acid. The acetic acid was deaerated by bubbling nitrogen through the liquid at reflux for 15 minutes. To the acetic acid at reflux was added 10.60 g (0.0740 mole) of $Cu_2O$ and the resulting suspension was refluxed for 20 minutes. At the end of this period, almost all of the $Cu_2O$ has dissolved and a blue-green solution had developed. To the solution at reflux was then added 100 g (0.368 mole) of 3-ethynyl-p-toluene sulfonate. Upon addition of the tosylate, the solution changed to orange in color. Heating was continued for an additional 1.5 hours. The reaction mixture was cooled, filtered and added dropwise to a stirring suspension consisting of 2500 ml $H_2O$, 300 g $NaHCO_3$, and 200 ml $CH_2Cl_2$. When all the bicarbonate appeared to have reacted, additional solid sodium bicarbonate was added as needed until all the acetic acid reaction mixture had been neutralized. The $CH_2Cl_2$ layer was then separated and the water layer was washed with 100 ml additional $CH_2Cl_2$. The 300 ml $CH_2$ layer was washed with two 500 ml portions of $H_2O$, dried with $MgSO_4$ and reduced in volume to approximately 80 ml of thick viscous oil which was chromatographed on a 60 × 5 cm dry column (quartz) of silica gel using 2:1 $CH_2Cl_2$-hexane as the eluent. The solvent was evaported to give 66.0 g (65% yield) of a white crystalline solid (m.p. 138°–139° C.)

Analysis Calc'd for $C_{30}H_{24}O_6S_2$: C,66.15; H,4.44. Found: C,65.82; H,4.13.

b. 1,4-Bis-(3-hydroxyphenyl)-buta-1-ene-3-yne.

To a 5 liter, 3-necked round bottom flask equipped with a nitrogen inlet and a distillation apparatus was added 125.0 g (0.23 mole) of 1,4-bis-[p-toluene sulfonate)]-3-yl-buta-1-ene-3-yne and 2500 ml of methanol. To the resulting pale yellow suspension was added 51.60 g NaOH in 750 ml of $H_2O$. The reaction mixture was then heated to reflux and about 2500 ml of distillate was collected. After removal of the methanol, 750 ml of $H_2O$ was added and the resulting solution was poured into a mixture of 400 ml of $H_2SO_4$ and 400 g of ice. The reaction mixture was then stirred until all the ice melted and the resulting precipitate filtered, washed with $H_2O$, air dried for a short time and then dried under high vacuum at room temperature for 24 hours. The solid was recrystallized by stirring in 1000 ml boiling cyclohexane and adding benzene slowly until solution occurred. The purple solution was treated with charcoal, filtered and cooled. The resulting crystals were filtered, air dried for a short time, and dried for 4 hours under high vacuum. A 3.0 g portion of the dried off-white solid was dissolved in 20 ml of 4:1 methylene chloride-acetonitrile and chromatographed on a 60×5 cm dry column (quartz), using 4:1 methylene chloride-acetonitrile as the eluent. The elution was followed by uv light and the large second band was collected. After removal of the solvent under reduced pressure, the resulting white solid (2.3 g) had a melting point of 146°–147° C.

Analysis Calc'd for $C_{16}H_{12}O_2$: C,81.33; H,5.12. Found: C,81.27; H,4.95.

EXAMPLE II

Poly[(E)-(oxy-1,4-phenylenesulfonyl-1,4-phenyleneoxy-1,3-phenylene-1-butene-3-ynylene-1,3-phenylene)] where X=Cl; a=1, b=0

In a 100 ml, 4-necked polymerization flask equipped with a magnetic stirring bar, a nitrogen inlet, an addition funnel, and a short-path distillation apparatus, were placed 0.5907 g (0.0025 mol) of 1,4-bis(3-hydroxyphenyl)-buta-1-ene-3-yne, 50 ml of a 0.1000 N solution of potassium hydroxide in methanol and 15 ml of benzene. The reaction mixture was heated by means of an oil bath and all but a few ml of the solvent distilled off. To the viscous liquid that remained was added 15 ml of additional benzene and distillation continued until the salt of the bis phenol began to precipitate on the side of the polymerization vessel. The temperature of the heating bath was 95° C. at this time. To the precipitated salt was added 12 ml of distilled sulfolane and 15 ml of additional benzene. The bath temperature was slowly raised to 130° C. during which time the benzene was distilled off and the salt dissolved in the sulfolane. Dichlorodiphenylsulfone (0.7179 g, 0.0025 mol) was then added and rinsed in with a few ml of dry benzene. The reaction mixture immediately turned bright red-orange in color. The temperature of the bath was then raised to 135°–140° C. and maintained there for 45 minutes. The temperature of the bath was then raised to 135°–140° C. and maintained there for 1 ½ hours. The reaction mixture was cooled, diluted to approximately 30 ml with methylene chloride, and precipitated into 1500 ml of methanol. The white fluffy polymer was filtered, air dried, and reprecipitated from methylene chloride-methanol to give 0.8 g of material which showed an intrinsic viscosity in N,N-dimethylacetamide of 0.38 at 30° C.

Analysis Calc'd for $(C_{28}H_{18}O_4S)_n$: C,76.64; H,4.03. Found: C,75.85; H,3.98.

EXAMPLE III

Poly[(E)-(oxy-1,4-phenylenesulfonyl-1,4-phenyleneoxy-1,3-phenylene-1-butene-3-ynylene-1,3-phenylene)] where X=F; a=1, b=0

In a 100 ml, 4-necked polymerization flask equipped with a magnetic stirring bar, a nitrogen inlet, an addition funnel, and a short-path distillation apparatus, were placed 0.5907 g (0.0025 mol) of 1,4-bis(3-hydroxyphenyl)-buta-1-ene-3-yne, 50 ml of a 0.1000 N solution of potassium hydroxide in methanol and 15 ml of benzene. the reaction mixture was heated by means of an oil bath and all but a few ml of the solvent distilled off. To the viscous liquid that remained was added 15 ml of additional benzene and distillation continued until the salt of the bis phenol began to precipitate on the side of the polymerization vessel. The temperature of the heating bath was 95° C. at this time. To the precipitated salt was added 12 ml of distilled sulfolane and 15 ml of additional benzene. The bath temperature was slowly raised to 130° C. during which time the benzene was distilled off and the salt dissolved in the sulfolane. Difluorodiphenylsulfone, 0.6357 g (0.0025 mol) was then added and rinsed in with a few ml of dry benzene. The reaction mixture immediately turned bright red-orange in color. The temperature of the bath was then raised to 135°–140° C. and maintained there for 15 minutes at which time a very viscous solution was obtained. The reaction mixture was cooled, diluted to approximately 40 ml with methylene chloride and precipitated into 1500 ml of methanol. The white fluffy polymer was filtered, air dried, and reprecipitated from methylene chloride-methanol to give 0.6 g of material which showed an intrinsic viscosity in N,N-dimethylacetamide of 0.67 at 30° C.

Analysis Calc'd for $(C_{28}H_{18}O_4S)_n$: C,76.64; H,4.03. Found: C,76.34; H,3.82.

EXAMPLE IV

Poly[(E)-(oxy-1,4-phenylenesulfonyl-1,4-phenyleneoxy-1,3-phenylene-1-buten-3-ynylene-1,3-phenylene)-co-(oxy-4,4'-biphenylene-oxy-1,e-phenylsulfonyl-1,4-phenylene)] where X=F, Ar=4,4'-Biphenylene, a=0.25, b=0.75

To a 50 ml polymerization flask equipped with a nitrogen inlet, an addition funnel, and a short path distillation apparatus was added 0.147 g (0.625 mmole) of 1,4-bis(3-hydroxyphenyl)-buta-1-ene-3-yne, 0.349 g (1.875 mmole) of 4,4'-dihydroxybiphenyl, 5.0 ml of 1N potassium hydroxide in methanol, 10 ml of methanol and 10 ml of benzene. The reaction mixture was heated and the solvent removed until only a few ml remained. At this time 10 ml of additional benzene was added and distilled to remove the last traces of water. To the resulting suspension was added 10 ml of dry dimethylsulfoxide and 10 ml of sulfolane. The temperature of the reaction mixture was slowly raised to 130° C. at which time all suspended solids went into solution. To the brownish orange solution was added 0.635 g (2.5 mmole) of 4,4'-difluorodiphenylsulfone and the solid was washed in with 5 ml dry benzene. The temperature was raised to 140°-145° C. and maintained at that temperature for 4 hours. The polymerization mixture was then cooled to room temperature and precipitated into 1500 ml of methanol. The white fluffy material was washed with methanol, air dried, dissolved in 20 ml of methylene chloride, filtered, and reprecipitated into methanol. A 0.5% solution of the polymer in N,N-dimethylacetamide at 30° C. gave an intrinsic viscosity of 0.74.

Analysis Calc'd for $(C_{52}H_{34}O_8S_2)_n$: C,72.77; H,4.03. Found: C,72.38; H,3.75.

EXAMPLE V

Poly[(E)-(oxy-1,4-phenylenesulfonyl-1,4-phenyleneoxy-1,3-phenylene-1-butene-3-ynylene-1,3-phenylene)-co-(oxy-4,4'-biphenyleneoxy-1,4-phenylsulfonyl-1,4-phenylene)] where X=F; Ar=4,4'-Biphenylene; a=0.5, b=0.5

To a 50 ml polymerization flask equipped with a nitrogen inlet, an additional funnel, and a short path distillation apparatus was added 0.295 g (1.25 mmole) of 1,4-bis(3-hydroxyphenyl)-buta-1-ene-3-yne, 0.233 g (1.25 mmole) of 4,4'-dihydroxybiphenyl, 5.0 ml of 1N potassium hydroxide in methanol, 10 ml of methanol and 10 ml of benzene. The reaction mixture was heated and the solvent removed until only a few ml remained. To the mixture 10 ml of additional benzene was added to azeotrope the last traces of water. To the resulting thick suspension was added 12 ml of dry dimethylsulfoxide and 6 ml of sulfolane. The temperature was slowly raised to 130° C. to obtain a homogeneous solution. To the solution was added 0.635 g (2.5 mmole) of 4,4'-difluorodiphenylsulfone. The temperature was increased to 140°-145° C. and maintained there for 4 hours. The polymerization mixture was then cooled to room temperature and precipitated into 1500 ml of methanol. The polymer was isolated, washed with methanol, air dried, dissolved in 20 ml methylene chloride, and reprecipitated into methanol. A 0.5% solution of the polymer in N,N-dimethylacetamide at 30° C. exhibited an intrinsic viscosity of 0.41.

Analysis Calc'd for $(C_{52}H_{34}O_8S_2)_n$: C,73.47; H,4.03. Found: C,73.05; H,4.35.

EXAMPLE VI

Poly[(E)-(oxy-1,4-phenylenesulfonyl-1,4-phenyleneoxy-1,3-phenylene-1-buten-3-ynylene-1,3-phenylene)-co-(oxy-4,4'-biphenyleneoxy-1,4-phenylsulfonyl-1,4-phenylene)] where X=F; Ar=4,4'-Biphenylene; a=0.10; b=0.90

To a 50 ml polymerization flask equipped with a nitrogen inlet, an additional funnel, and a short path distillation apparatus was added 0.059 g (0.25 mmole) of 1,4-bis(3-hydroxyphenyl)-buta-1-ene-3-yne, 0.419 g (2.25 mmole) of 4,4'-dihydroxyphenyl, 5.0 ml of 1N potassium hydroxide in methanol, 10 ml of additional methanol and 10 ml of benzene. The reaction mixture was heated and the solvent removed until only a few ml remained. At this time 10 ml of additional benzene was added and distilled to remove the last traces of water. To the suspension was added 12 ml of dry dimethylsulfoxide and 10 ml of dry sulfolane. The temperature of the reaction mixture was slowly raised to 120° C. during which time all suspended solids in the reaction mixture went into solution. To the homogeneous solution was added 0.635 g (2.5 mmole) of 4,4'-difluorodiphenylsulfone and the solid was washed in with 5 ml of dry benzene. The temperature was raised slowly to 140°-145° C. and maintained at that temperature for 4 hours. The polymerization mixture was allowed to cool to room temperature and precipitated into 1500 ml of methanol. The polymer was washed with methanol, air dried, dissolved in 20 ml of methylene chloride, and reprecipitated into methanol. A 0.5% solution of the polymer in N,N-dimethylacetamide at 30° C. exhibited an intrinsic viscosity of 0.44.

Analysis Calc'd for $(C_{52}H_{34}O_8S_2)_n$: C,72.31; H,4.03. Found: C,71.95; H,3.85.

EXAMPLE VII

Cure reactions of Polymers of Examples II, IV, V and VI

Samples of neat polymer prepared in Examples II, IV, V and VI were cast from methylene chloride into 1 mil film specimens. The glass transition temperatures of the films were determined by differential scanning calorimetry at 20° C./min. The data obtained are shown below in the table. The film specimens were then placed in a preheated oven at 343° C. (650° F.) and removed and allowed to cool to room temperature. The glass transition temperatures of the cured polymers were then redetermined as above (table). After cure, the film specimens were completely insoluble in the casting solvent, as well as in all other solvents tested. Film specimens could also be rendered insoluble by exposing them to uv radiation or sunlight for 1 to 2 hours. Films of Example II were also cast from methylene chloride containing an equal molar amount of monofunctional acetylene compound 4-chloro-4'-(3-ethynylphenoxy)-diphenylsulfone (reactive plasticizer) and thermally treated as above. The glass transition temperatures of the mixture before and after cure are also set forth in the table.

TABLE

| Polymer | Value of (a) | Value of (b) | Tg, °C. Before Cure | Tg, °C. After Cure |
|---|---|---|---|---|
| II | 1 | 0 | 179 | None, obs. |
| II | — (reactive plasticizer) | | 89 | 310 |
| IV | .25 | .75 | 205 | 255 |
| V | .50 | .50 | 191 | 287 |
| VI | .10 | .90 | 214 | 234 |

As seen from the foregoing, the glass transistion temperatures of the enyne polysulfone thermoplastics increase as a result of thermal treatment (curing). Thus, lower Tg's are provided for fabrication while after curing the Tg's increase to give high use temperatures. By using a monofunctional acetylene compound (reactive plasticizer) with the enyne polysulfones, the Tg's of the thermoplastics are decreased, thereby permitting the use of low processing temperatures. However, during curing the reactive plasticizer becomes dormant and the Tg's of the thermoplastics increase to produce high use temperatures. The enyne polysulfones become lightly crosslinked during curing, thereby rendering the polymers solvent resistant. Because of their outstanding properties, the thermoplastic polymers of this invention are eminently suitable for use in the fabrication of fiber-reinforced composites.

As will be evident to those skilled in the art, modifications of the present invention can be made in view of the foregoing disclosure without departing from the spirit and scope of the invention.

We claim:

1. An enyne polysulfone consisting of essentially repeating units having the following structural formula:

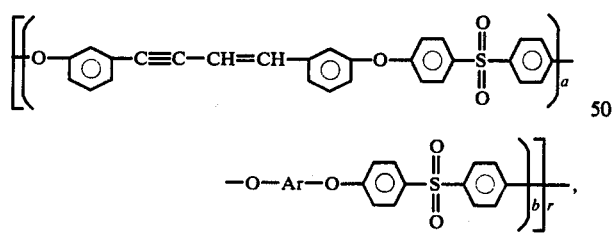

wherein Ar is a divalent aromatic radical; a is equal to 0.05 to 1, b is equal to zero to 0.95, and the sum of a and b is equal to 1; and n is an integer ranging from about 1 to 100.

2. The enyne polysulfone according to claim 1 in which Ar is

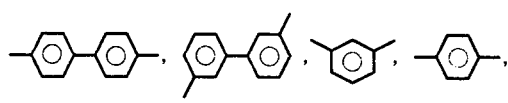

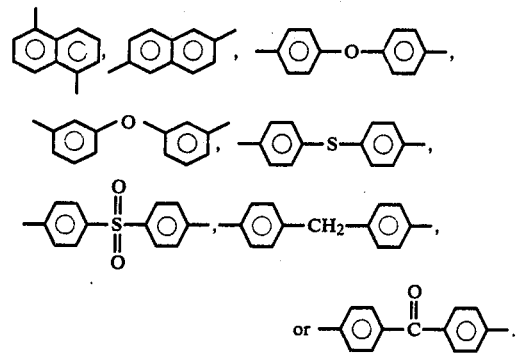

3. The enyne polysulfone according to claim 2 in which Ar is

4. The enyne polysulfone according to claim 2 in which Ar is

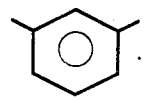

5. The enyne polysulfone according to claim 2 in which Ar is

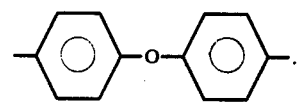

6. The enyne polysulfone according to claim 2 in which Ar is

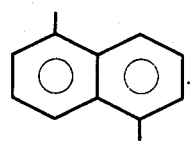

7. The enyne polysulfone according to claim 2 in which Ar is

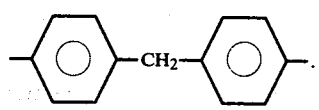

8. A composition comprising (1) an enyne polysulfone consisting essentially of repeating units having the following structural formula:

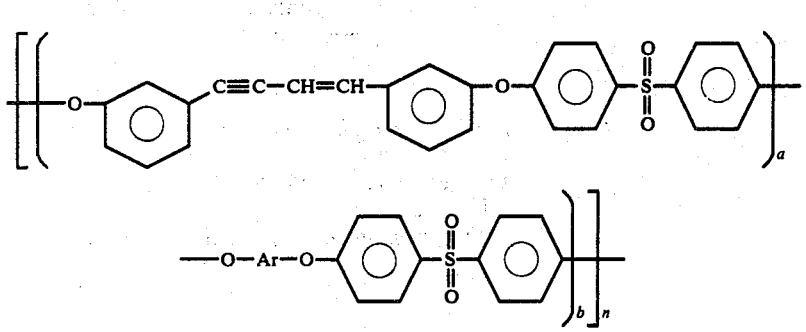

wherein Ar is

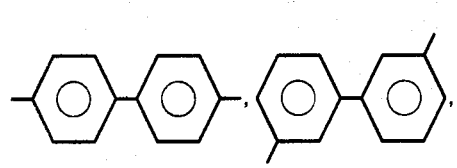

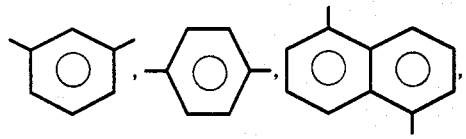

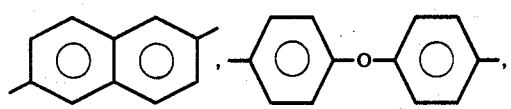

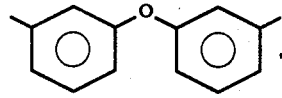

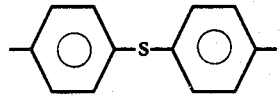

a is equal to 0.05 to 1, b is equal to zero to 0.95, and the sum of a and b is equal to 1; and n is an integer ranging from about 1 to 100; and (2) a monofunctional acetylene compound having the following structural formula:

R—C≡CH, wherein R is $C_xH_{2x+1}$, where x is an integer from 1 to 10, inclusive,

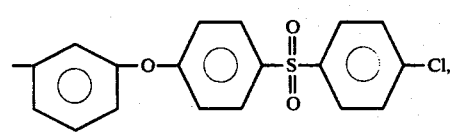

-continued

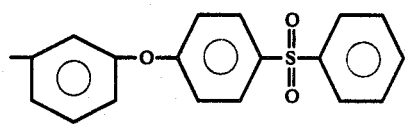

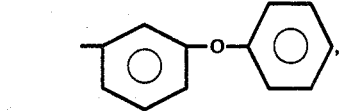

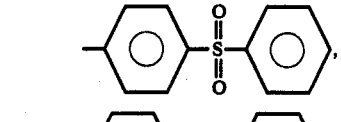

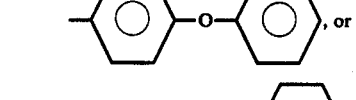

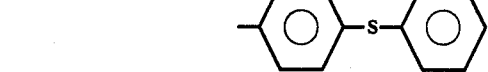

the amount of the acetylene compound ranging from about 10 to 90 mole percent of the amount of enyne in the polysulfone structure.

9. A process for preparing enyne polysulfones which comprises the following steps:
(a) reacting an alkali metal hydroxide with (1) 1,4-bis(3-hydroxyphenyl)-buta-1-ene-3-yne alone or in admixture with (2) an aromatic diol, thereby forming an alkali metal salt of compound (1) or a mixture of alkali metal salts of compounds (1) and (2), compound (2) having the following formula:

HO—Ar—Oh, wherein Ar is a divalent aromatic radical selected from the groups of radicals consisting of

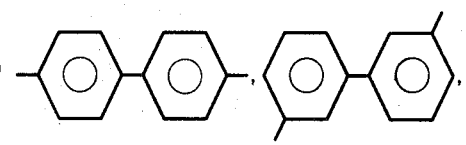

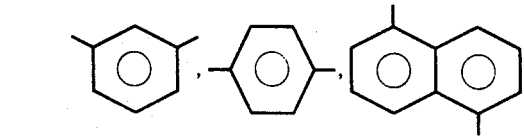

-continued
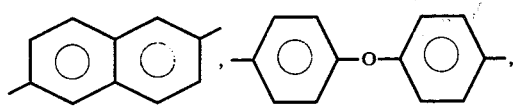
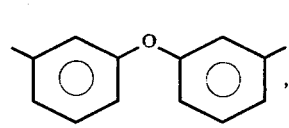
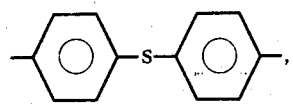
-continued
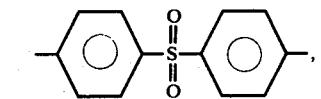
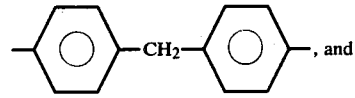
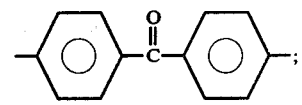
(b) reacting in an aprotic solvent the alkali metal salt or mixture of alkali metal salts formed in step (a) with an equimolar amount of 4,4'-dihalodiphenylsulfone; and
(c) recovering an enyne polysulfone product.
* * * * *

UNITED STATES PATENT AND TRADEMARK OFFICE
CERTIFICATE OF CORRECTION

PATENT NO. : 4,178,428
DATED : December 11, 1979
INVENTOR(S) : Fred E. Arnold and Bruce A. Reinhardt It is certified that error appears in the above-identified patent and that said Letters Patent are hereby corrected as shown below:

Col. 4, line 49, change "dio" to -- diol --. Col. 7, line 29, change "$CH_2$" to -- $CH_2Cl_2$ --. Col. 11, line 10, change "-(reactive plasticizer)" to -- +(reactive plasticizer)--. Col. 11, line 41, change "of essentially" to -- essentially of --. Col. 11, line 54, after last bracket, change "r" to -- n --.

Signed and Sealed this

Eighth Day of April 1980

[SEAL]

Attest:

SIDNEY A. DIAMOND

Attesting Officer

Commissioner of Patents and Trademarks